United States Patent [19]

Tyson

[11] 4,081,150
[45] Mar. 28, 1978

[54] MULTI-PURPOSE THERAPEUTIC PAD

[76] Inventor: Gordon Tyson, 256 Betty Ann Dr., Willowdale, Ontario, Canada

[21] Appl. No.: 756,820

[22] Filed: Jan. 5, 1977

[51] Int. Cl.² .............................................. A61F 7/00
[52] U.S. Cl. .................................. 128/402; 128/403; 128/DIG. 15; 128/171
[58] Field of Search .............. 128/399, 402, 403, 171, 128/DIG. 15, 379, 384

[56] References Cited

U.S. PATENT DOCUMENTS

| 3,407,818 | 10/1968 | Costanzo | 128/384 |
| 3,561,442 | 2/1971 | Goswitz | 128/DIG. 15 |
| 3,882,867 | 5/1975 | Moran | 128/402 |
| 3,882,873 | 5/1975 | Arango | 128/379 |

*Primary Examiner*—Lawrence W. Trapp
*Attorney, Agent, or Firm*—Young & Thompson

[57] ABSTRACT

A multi-purpose therapeutic pad device includes a first strip of flexible material having opposed faces and free ends. Velcro fastening means are carried adjacent one of the free ends and a series of longitudinally spaced fastening elements are carried adjacent the other free end. A pouch member is formed integrally with the strip and projects from one of the faces thereof. The pouch member has inner and outer walls, the inner wall being common to the pouch member and the strip. A second strip of elastic material has a series of longitudinallly spaced fastening elements adjacent one of its free ends and Velcro fastening means adjacent the other free end. Such longitudinally spaced fastening elements and Velcro fastening means are cooperable with the corresponding longitudinally spaced fastening elements and Velcro fastening means on the first strip to releasably connect the first and second strip to releasably connect the first and second strips. The wall common to the first strip and pouch member is formed of an open mesh material so as to permit the application of heat or cold to the skin of a person upon whom the device is applied.

4 Claims, 2 Drawing Figures

4,081,150

MULTI-PURPOSE THERAPEUTIC PAD

BACKGROUND OF THE INVENTION

The present invention relates to a multi-purpose therapeutic pad device adapted to selectively apply heat or cold to the surface of a limb or torso of a person.

Therapeutic pads, bandages and the like have been known heretofore and have enabled persons to apply heat in controlled amounts to areas of the arms, legs and shoulders. U.S. Pat. No. 2,617,916 issued Nov. 11, 1952, for example, discloses a heating pad in the form of a sleeve which can be wrapped about an arm, leg or other body part. The device includes a composite pad having inner and outer fabric layers between which a coil of insulated resistance wire is interposed. U.S. Pat. No. 2,712,591 issued July 5, 1955 to A. S. Rogell discloses an electrical bandage in which electrical strips of Nichrome ribbon are positioned between neoprene strips. There has been no convenient device available heretofore, to applicant's knowledge, by means of which one may apply either heat or cold to the surface of a limb or torso or which will provide security against the shifting of the device from its intended position over the injured area due to movement of the wearer.

SUMMARY OF THE INVENTION

It is the primary object of the invention to provide a multi-purpose therapeutic pad which is adjustable in size so as to accommodate a person's limb or torso for the application of heat or cold thereto.

It is another object of the invention to provide a multi-purpose therapeutic pad of the character described which, once adjusted in position over the area to be treated, will remain in position despite the person's movement.

Other objects and advantages of the invention will become readily apparent from the following description of the invention.

According to the present invention there is provided a multi-purpose therapeutic pad device comprising in combination: a first strip of flexible material having first and second opposed faces and a pair of free ends, a series of longitudinally spaced fastening elements carried by the strip adjacent one of the free ends, and Velcro fastening means on one face of the strip adjacent the other of the free ends; a pouch member integral with the strip and projecting from one of the faces intermediate the free ends, the pouch member including inner and outer walls and the inner wall being common to the strip and pouch member; and a second strip of elastic material having a series of longitudinally spaced fastening elements adjacent one free end thereof cooperable with selected fastening elements on the first strip for releasably connecting the one free end of the first and second strips, Velcro fastening means being provided on the second strip adjacent the other free end thereof cooperable with the Velcro fastening means on the first strip for releasably connecting the other free ends of the first and second strips.

BRIEF DESCRIPTION OF THE DRAWING

In order that the invention may be more fully comprehended it will now be described, by way of example, with reference to the accompanying drawings, in which.

DETAILED DESCRIPTION OF THE INVENTION

Figure 1:
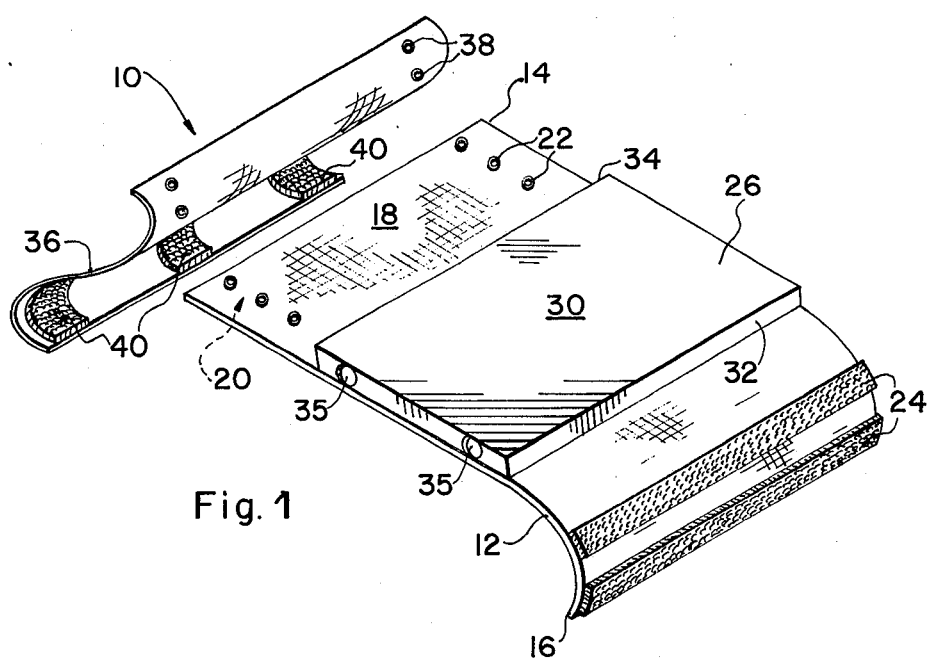
FIG. 1 is a perspective view of the therapeutic pad device embodying the features of the invention.
Figure 2:
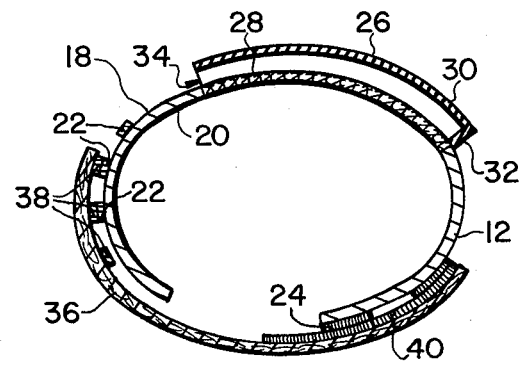
FIG. 2 is a cross-sectional view of the device shown in FIG. 1 applied to the limb of a person.

Referring to the drawings, there is shown generally, as indicated by reference numeral 10, a therapeutic pad device. The device includes a first strip 12 of a flexible material which may be a textile fabric, leather or any material capable of sufficient flexure such that it can be wrapped about a limb or the torso of a person when the device is placed in use. As can be seen most clearly from FIG. 1, strip 12 has a pair of opposed free ends 14, 16 and opposed faces 18, 20. A series of longitudinally spaced fastening elements 22 are provided on the strip adjacent the free end 14. One or more bands 24 of Velcro are provided at the other free end 16.

Intermediate the free ends of the strip there is formed integrally therewith a pouch member 26. The pouch member projects outwardly from the face 18 of the strip and includes inner and outer walls 28, 30 as well as a bottom wall enclosure 32. The end of the pouch opposite to that of the bottom wall is desirably open to afford an entrance opening 34. However, it is within the contemplation of the invention to provide the pouch with a flap-type cover if so desired. The inner wall of the pouch member is common to both the strip and the pouch member and is formed of an open mesh material so as to facilitate the transmission of heat therethrough to the underlying surface of the of the limb or torso about which the pad 10 is wrapped. The porous characteristic of the inner wall is equally important in connection with the use of cold and/or wet compresses, to the underlying epidermal area. Thus, inner wall 28 may comprise a gauze bandage-type material or may simply comprise the flexible material from which the remainder of the strip is formed. In the latter instance, however, there must be adequate openness of structure to afford the desired porosity. One or more apertures 35 are desirably formed in one of the outer walls of the pouch to permit drawing of the usual electric cord therethrough for connection of the standard heating pad, which may be positioned within pouch 26, with a source of electricity. Such apertures may be grommeted to provide improved strength.

A second strip 36 is provided of an elastic material such as one of the conventional stretch textile fabrics. Adjacent one end of the strip there is provided a series of longitudinally spaced fastening elements 38 which are cooperable with fastening elements 22 on strip 12. The spacing between the fastening elements on strips 12 and 36 are desirably the same although this is not essential. Preferably fastening elements 22 and 38 comprise conventional male and female snap elements. The other end of strip 36 is given one or more Velcro bands 40 adapted to cooperate with the Velcro bands 24 on strip 12. As shown most clearly in FIG. 1, the Velcro bands 40 may extend longitudinally of strip 36 and the Velcro bands 24 may extend transversely of strip 12. The arrangement of the Velcro bands in this manner affords a greater range of adjustability in the size of the therapeutic pad while assuring optimum securement between the strips 12 and 36 at the ends of such strips where the Velcro bands are located. The strip 36 is preferably not as long as strip 12 but is desirably of the same width.

From the foregoing description it will be seen that a therapeutic pad device has been provided which is of relatively simple construction but nevertheless can serve equally well in situations where heat or cold, wet or dry application is to be utilized. Due to the arrangement of the Velcro bands and the spaced fastening elements in conjunction with the stretch elastic material of strip 36 the device can be applied to an arm, leg or to the torso of an individual with assurance that the injured area to be treated will be properly covered and subjected to the desired therapeutic treatment. Also, there is minimal possibility of the device shifting from the desired position due to movement of the person wearing the device.

I claim:

1. A multi-purpose therapeutic pad device comprising in combination:

a first strip of flexible material having first and second opposed faces and a pair of free ends, a series of longitudinally spaced fastening elements carried by said strip adjacent one of said free ends, and Velcro fastening means on one face of said strip adjacent the other of said free ends;

a pouch member integral with said strip and projecting from one of said faces intermediate said free ends, said pouch member including inner and outer walls and the said inner wall being common to said strip and pouch member; and a second strip of elastic material having a series of longitudinally spaced fastening elements adjacent one free end thereof cooperable with selected fastening elements on said first strip for releasably connecting said one free end of said first and second strips, Velcro fastening means being provided on said second strip adjacent the other free end thereof cooperable with the Velcro fastening means on said first strip for releasably connecting said other free ends of said first and second strips.

2. A therapeutic pad device according to claim 1, wherein said common wall of said pouch member and first strip comprises an open mesh material.

3. A therapeutic pad device according to claim 1, wherein said longitudinally spaced fastening elements comprise mating male and female snap elements.

4. A therapeutic pad device according to claim 1, wherein the Velcro fastening means on one of said strips comprise bands which extend transversely thereof and the Velcro fastening means on the other of said strips comprise bands which extend longitudinally thereof.

* * * * *